(12) United States Patent
Xu et al.

(10) Patent No.: US 8,324,373 B2
(45) Date of Patent: Dec. 4, 2012

(54) HIGHLY STEREOSELECTIVE PROCESS FOR PREPARING GEMCITABINE AND INTERMEDIATES THEREOF

(75) Inventors: Yongxiang Xu, Nanjing (CN); Hao Yang, Nanjing (CN); Wen Hou, Nanjing (CN)

(73) Assignee: Nanjing Cavendish Bio-Engineering Technology Co., Ltd. (CN)

( * ) Notice: Subject to any disclaimer, the term of this patent is extended or adjusted under 35 U.S.C. 154(b) by 343 days.

(21) Appl. No.: 12/601,942

(22) PCT Filed: Sep. 7, 2007

(86) PCT No.: PCT/CN2007/002672
§ 371 (c)(1),
(2), (4) Date: Nov. 25, 2009

(87) PCT Pub. No.: WO2008/144970
PCT Pub. Date: Dec. 4, 2008

(65) Prior Publication Data
US 2010/0179314 A1    Jul. 15, 2010

(30) Foreign Application Priority Data

May 31, 2007  (CN) .......................... 2007 1 0106089

(51) Int. Cl.
| | | |
|---|---|---|
| C07H 19/00 | (2006.01) |
| C07H 21/00 | (2006.01) |
| C07H 1/00 | (2006.01) |
| C07H 3/00 | (2006.01) |
| C08B 37/00 | (2006.01) |
| A01N 43/04 | (2006.01) |
| A61K 31/70 | (2006.01) |
| C07D 237/00 | (2006.01) |
| C07D 237/02 | (2006.01) |

(52) U.S. Cl. ........ 536/28.5; 536/22.1; 536/124; 514/42; 514/43; 514/49; 544/224

(58) Field of Classification Search ............ 536/28.5, 536/22.1, 124; 514/42, 49; 544/224
See application file for complete search history.

(56) References Cited

U.S. PATENT DOCUMENTS

| | | |
|---|---|---|
| 4,526,988 A | 7/1985 | Hertel |
| 4,808,614 A | 2/1989 | Hertel |
| 5,371,310 A | 12/1994 | Bennett et al. |
| 5,401,838 A | 3/1995 | Chou |
| 5,401,861 A | 3/1995 | Chou |
| 5,606,048 A | 2/1997 | Chou et al. |
| 2008/0058509 A1* | 3/2008 | Lee et al. ............ 536/22.1 |

FOREIGN PATENT DOCUMENTS

| | | |
|---|---|---|
| EP | 0577303 | 10/1997 |
| JP | 6157570 A | 6/1994 |
| JP | 8239374 A | 9/1996 |
| WO | 2006/009353 | 1/2006 |
| WO | 2006/011713 | 2/2006 |
| WO | 2007027564 A2 | 3/2007 |

OTHER PUBLICATIONS

World Intellectual Property Organization, "International Search Report" for PCT/CN2007/002672, mailed Feb. 28, 2008. This U.S. application is a national-phase application of of PCT/CN2007/002672 (4 pages).

* cited by examiner

*Primary Examiner* — Scarlett Goon
(74) *Attorney, Agent, or Firm* — Kolisch Hartwell, P.C.

(57) ABSTRACT

The present invention provides a novel and highly stereoselective process for preparing gemcitabine, which is suitable for industrial production, wherein, it includes the following reactions. Additionally, the invention discloses the key intermediates. The definition for the groups of G1, G2, G3, G4, and G5 are described in the specification.

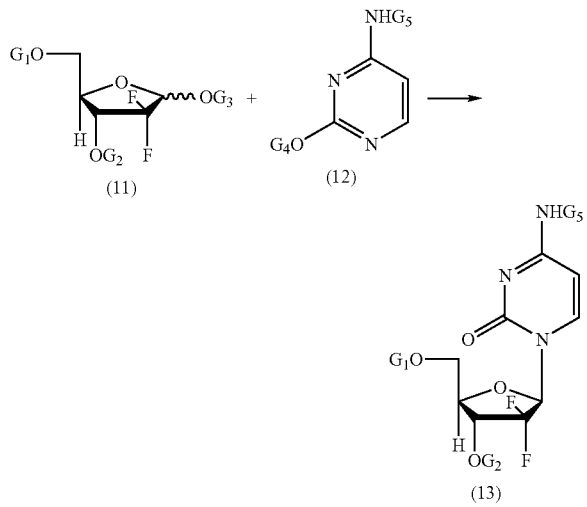

8 Claims, 10 Drawing Sheets

HIGHLY STEREOSELECTIVE PROCESS FOR PREPARING GEMCITABINE AND INTERMEDIATES THEREOF

FIELD OF THE INVENTION

This invention relates to a process for chemically preparing antineoplastic nucleotides as antimetabolites, more particularly, to a highly stereoselective process for preparing qemcitabine and intermediates thereof.

BACKGROUND OF THE INVENTION

Gemcitabine, a water soluble analogue of deoxycytidine, is an antineoplastic agent of difluoronucleotides by destroying cellular duplications, and a substitution in consistent with substrates activated by ribonucleotide reductases, which are vital in the syntheses of desired deoxynucleotides during the process of DNA synthesizing and repairing.

Gemcitabine is 2'-deoxy-2',2'-difluorocytidine, and its chemical structure is the following:

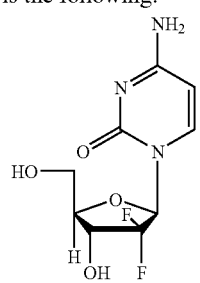

Hertel et al firstly disclosed the gemcitabine compound in the U.S. Pat. No. 4,808,614 and described the preparing scheme thereof:

In the scheme, only the step of synthesizing ethyl 2,2-difluoro-3-hydroxy-3-(2,2-dimethyl-dioxolan-4-yl)-propionate involved applying silica gel column chromatography to separate the 3-R-hydroxy product, the reactions of the following steps had not been involved to the stereochemistry.

Chou Ta-Sen described another preparing scheme in U.S. Pat. No. 5,401,861 and European patent No. 0577303, in which, alpha-anomer enriched 2-deoxy-2,2-difluoro-D-ribofuranosyl-3,5-di-O-benzoyl-methanesulfonate was firstly prepared, then yielded beta-anomer enriched gemcitabine. The characteristic of the reaction for preparing alpha-anomer enriched methanesulfonate intermediate proceeded in the lower temperature (−78° C.), followed by reacting with more than 3-20 times (mols) of silyl protected cytosine, to stereoselectively produce beta-anomer enriched gemcitabine product. It should be noted that only benzoyl was disclosed as 3,5-hydroxyls protected group in these two patents. Furthermore, the reaction for preparing alpha-anomer enriched methanesulfonate was achieved in very low temperature, a more rigorous reaction condition, which is not suitable for large scale industrial application.

In addition, Lee Jaeheon et al disclosed the following scheme for preparing the intermediates in the patent international application WO2006/009353:

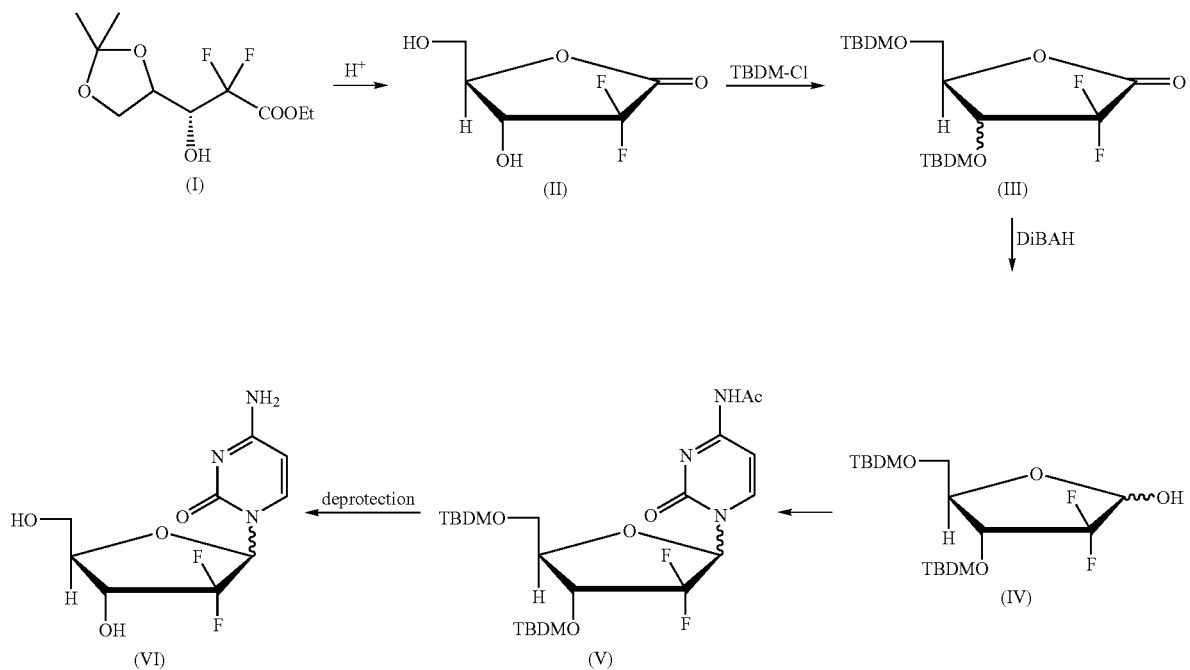

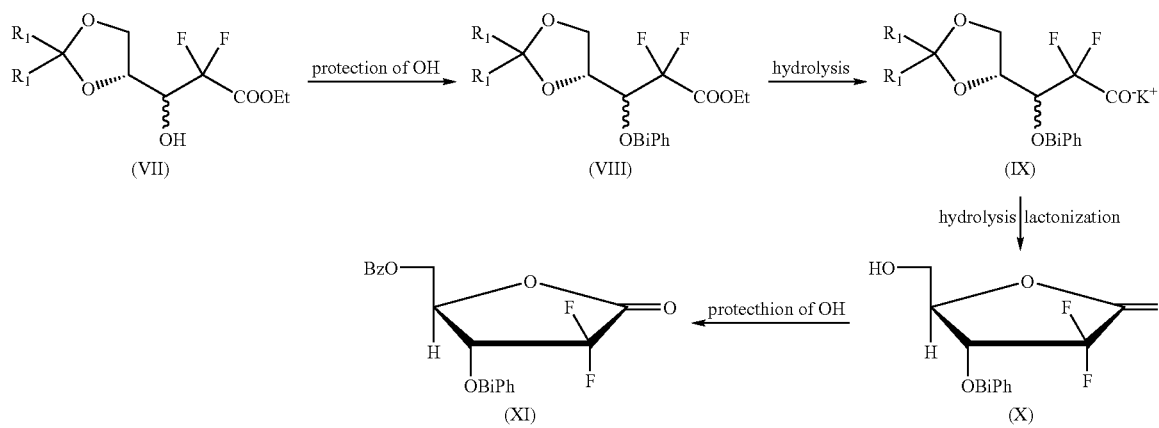

Moreover, Lee Jaeheon et al described the following scheme in the patent international application WO2006/011713:

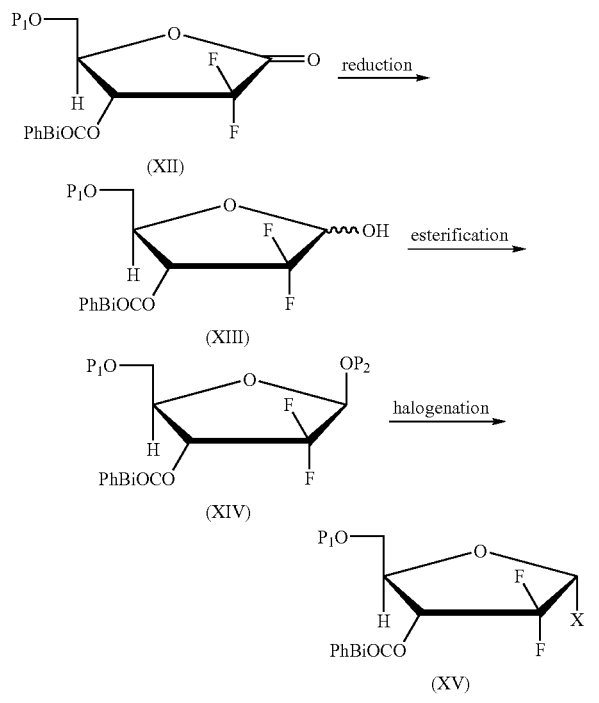

Wherein, $P_1$ is Bz or BiPhC(O)—, $P_2$ is —P(O)(OPh)$_2$. The alpha-anomer enriched halogenated intermediates were achieved by the above-mentioned reactions, and provided useful intermediates for stereoselectively preparing gemcitabine. However, it is found by our experiments that, in the said process of WO2006/009353, the work-up procedure of the prepared potassium salts compound requires the organic solvent of reactant solution to be rapidly concentrated to dryness under the low temperature, otherwise the product (potassium salt) would be seriously decomposed. This would affect the purity and yield, which would be too difficult to be achieved in the industrial operations. Furthermore, the excessive amount of toxic hydrogen halides that were needed in the halogenation process, posed safety problem to workers' labor protection, difficulty of handling the wastes, and vulnerability to environmental pollution.

In conclusion, the processes for preparing gemcitabine in the prior art are still insufficient as mentioned above. At present, a big demand is in need to develop a highly stereoselective process for preparing gemcitabine, in which the reaction conditions are mild and friendly to the environment.

DESCRIPTIONS OF THE INVENTION

During investigating the processes for preparing gemcitabine, the inventors of the present invention have surprisingly discovered a novel process for preparing gemcitabine, which overcomes the disadvantage of the prior art, and produces gemcitabine or its hydrochloride salt in high stereoselectivity and good yield therefrom.

In accordance with the object of the present invention, there is provided a highly stereoselective process for preparing gemcitabine.

In another aspect, the present invention provides the intermediates for preparing gemcitabine.

Specifically, the present invention provides a process for preparing gemcitabine, which includes the following reaction:

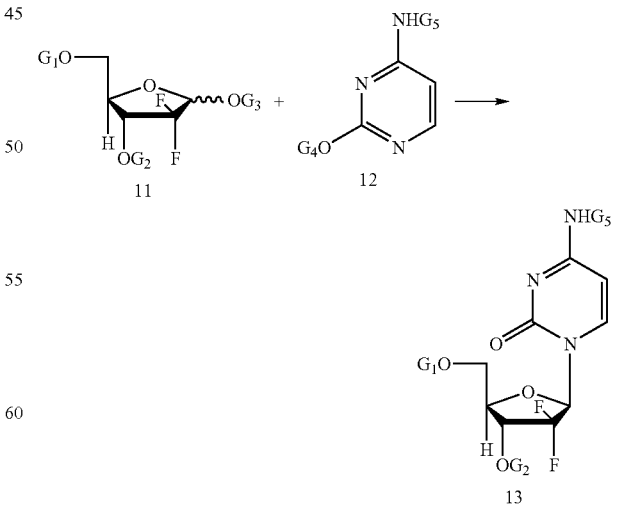

wherein, the substitutions of G1 and G2 are independently the radicals defined by the following structure:

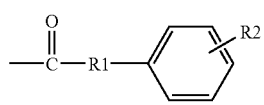

wherein, R1 is selected from the group consisting of C1-C3 alkyl and null (i.e. the ring of benzene is directly linked to the carbonyl), preferably null, or —CH₂—, or —CH₂CH₂—;

R2 is selected from the group consisting of hydrogen, C1-C4 alkyl, phenyl and the substituted phenyl;

and with the provision that at least one of R2 in the G1 and G2 is phenyl or substituted phenyl;

the said substituted phenyl is the one substituted by C1-C4 alkyl, or halogen (fluorine, chlorine, bromine, iodine);

G3 is selected from the group consisting of alkylsulfonyl, arylsulfonyl, substituted alkylsulfonyl and substituted arylsulfonyl, preferably, methylsulfonyl, ethylsulfonyl, benzylsulfonyl, toluenesulfonyl, and p-nitrobenzenesulfonyl;

G4 and G5 are independently selected from the group consisting of C1-C7 trialkylsilyl, preferably, trimethylsilyl, isopropyldimethylsilyl, methyldiisopropylsilyl, triisopropylsilyl or t-butyldimethylsilyl, more preferably, trimethylsilyl; t-butoxycarbonyl, carbobenzoxy) or 9-fluorenylmethoxycarbonyl (Fmoc); and formyl, acetyl, propionyl, isopropionyl, butyryl, isobutyryl, pivaloyl, and the likes;

preferably, the said reaction is that the alpha-anomer enriched formula 11 compound is reacted with formula 12 compound to obtain beta-anomer enriched formula 13 compound.

More specifically, the said reaction means that certain molar ratio of formula 12 compound to the alpha-anomer enriched formula 11 compound is dissolved in the organic solvent, and heated to 40~300° C., then the solution of the alpha-anomer enriched formula 11 compound dissolved in the organic solvent is added dropwise thereto within 20 hours, after the addition, maintains the temperature and reacts for 10~20 mins, to furnish beta-anomer enriched formula 13 compound;

the said certain molar ratio is referred to formula 12 compound relative to the formula 11 compound, and it is from 1 to 20, preferably, from 1.5 to 15;

the said alpha-anomer enriched formula 11 compound means the ratio of alpha:beta thereof is no less than 1:1;

the said organic solvent may be selected from inert solvent, it's boiling point is above 70° C., and be selected from the group consisting of alkyl halides, benzenes, ethers, and the likes, preferably, 1,2-dichloroethane, toluene, xylene, substituted benzene, anisole, diphenyl ether or substituted diphenyl ether, and the likes, one or more of mixture thereof;

whereas formula 12 compound is dissolved in the organic solvent, and heated to 40~250° C., the preferred temperature is from 100 to 150° C., more preferably from 110 to 150° C.;

whereas the formula 11 compound dissolved in the organic solvent is dropped within 20 hours, the preferred period of dropping is between 4 and 7 hours;

whereas after the dropping finished, maintains the temperature and keeps on the reaction for 10~20 mins, the preferred period of reaction is 3~6 hours;

more specifically, the embodiment of the present invention is: formula 12 compound (2.5 molar ratio, to the formula II compound) is dissolved in xylene, then warmed up to 100° C., and the solution of the alpha-anomer enriched formula II compound in xylene is added dropwise thereto within 3 hours, after the dropping finished, the mixture is warmed up and kept on the reaction for 10~20 mins to furnish beta-anomer enriched formula 13 compound;

the said reaction is that formula 12 compound (10 molar ratio, to the formula 11 compound) is dissolved in the toluene, stirred and heated to reflux, then the alpha-anomer enriched formula 11 compound in the toluene is added dropwise thereto within 3 hours, after complete dropping, maintaining the reaction for 5 hours to obtain the beta-anomer enriched formula 13 compound.

Herein, the process further includes that the compound 13 is deprotected into formula 2 compound:

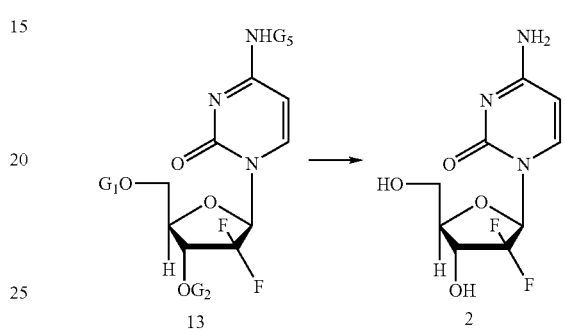

The reaction condition may be selected from: the formula 13 compound is added to a solution of dry methanol/ammonia solution, and the mixture reacts at 0° C.~65° C. for 1~30 hours with stirring, concentrated to dryness under vacuum, then water was added to dissolve the residue, and extracted with an organic solvent to remove organic impurities thereof, finally, the resulting aqueous phase is concentrated to dryness to furnish formula 2 compound.

The said solution of dry ammonia/methanol, it's concentration is preferred from 5% to 16%;

the said reacting temperature for 2~30 hours with stirring, it means, preferably, the reaction temperature is between 20~50° C. and the period of reaction is for 15~20 hours;

the mentioned organic solvent used to remove organic impurities thereof means that, the organic solvent is selected from any lower boiling-point solvents that are soluble in methyl benzoate and water-immiscible, preferably, dichloromethane, or ethyl acetate.

The process described herein further includes that the formula 2 compound reacts with hydrochloric acid to yield hydrochloride salt thereof.

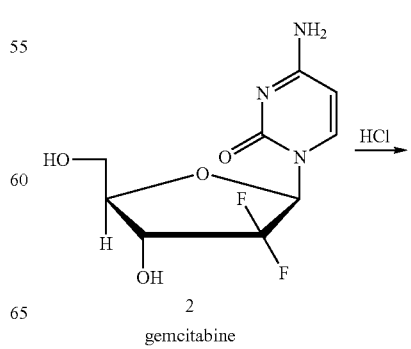

gemcitabine

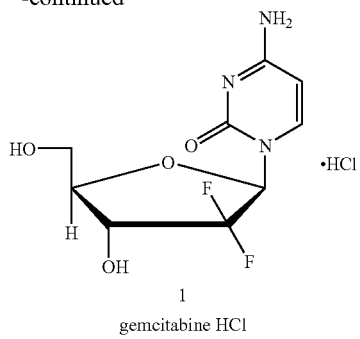

gemcitabine HCl

The reaction condition is that formula 2 compound is added to an organic solvent while at −10~50° C. Conc. hydrochloric acid was added dropwise to adjust the pH of the mixture between 1.5 and 2.5 and then let the crystal grow at the lower temperature from 10 mins to 8 hours. Next, filter and wash the filtered cake with an organic solvent to give gemcitabine hydrochloride;

herein, as described above as formula 2 compound is added to an organic solvent, the mentioned organic solvent is selected from any organic solvent which did not dissolve gemcitabine hydrochloride salt, preferably, methanol, ethanol, isopropyl alcohol, acetone, or a mixture thereof.

as described as to let the crystal grow at the lower temperature from 10 mins to 8 hours, the lower temperature is from −10 to 25° C., preferably, from 0 to 5° C.; the period for crystal is 2-5 hours.

In another aspect of this invention, the invention provides the following structural compound

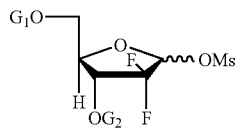

11 wherein, the substituents G1 and G2 independently are the group defined as the following structure:

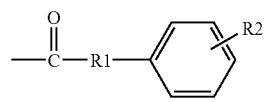

wherein, R1 is selected from the group consisting of C1-C3 alkyl, or null, preferably, null or —CH$_2$—, CH$_2$CH$_2$—;

R2 is selected from hydrogen, C1-C4 alkyl, phenyl or substituted phenyl;

preferably, G1 and G2 are independently selected from benzoyl, phenylacetyl, biphenylcarbonyl, and biphenylacetyl;

with the provision that at least one of G1 and G2 is selected from phenyl or substituted phenyl;

wherein, the substituted phenyl is phenyl substituted by C1-C4 alkyl, or halogen (fluorine, chlorine, bromine, iodine);

G3 is selected from the group consisting of alkylsulphonyl, arylsulphonyl, substituted alkylsulphonyl and substituted arylsulphonyl, preferably, methylsulphonyl, benzylsulphonyl, p-toluenesulphonyl and p-nitrobenzenesulphonyl.

The preferred intermediate compounds include:

2-deoxy-2,2-difluoro-D-arabinofuranose-3,5-di-(4-phenyl)benzoate-1-methanesulphonate;

2-deoxy-2,2-difluoro-D-arabinofuranose-3,5-di-(4-phenyl)benzoate-1-ethane sulphonate;

2-deoxy-2,2-difluoro-D-arabinofuranose-3,5-di-(4-phenyl)benzoate-1-benzenesulphonate;

2-deoxy-2,2-difluoro-D-arabinofuranose-3,5-di-(4-phenyl)benzoate-1-p-nitro benzenesulphonate;

2-deoxy-2,2-difluoro-D-arabinofuranose-5-benzoate-3-(4-phenyl)benzoate-1-methanesulphonate;

1α-2-deoxy-2,2-difluoro-D-arabinofuranose-3,5-di-(4-phenyl)benzoate-1-methanesulphonate;

1β-2-deoxy-2,2-difluoro-D-arabinofuranose-3,5-di-(4-phenyl)benzoate-1-methanesulphonate;

1α-2-deoxy-2,2-difluoro-D-arabinofuranose-5-benzoate-3-(4-phenyl)benzoate-1-methanesulphonate;

1β-2-deoxy-2,2-difluoro-D-arabinofuranose-5-benzoate-3-(4-phenyl)benzoate-1-methanesulphonate;

2-deoxy-2,2-difluoro-D-arabinofuranose-5-benzoate-3-(4-phenyl)benzoate-1-ethanesulphonate;

2-deoxy-2,2-difluoro-D-arabinofuranose-5-benzoate-3-(4-phenyl)benzoate-1-benzylsulphonate;

2-deoxy-2,2-difluoro-D-arabinofuranose-5-benzoate-3-(4-phenyl)benzoate-1-p-nitrobenzenesulphonate.

Additionally, the intermediates provided in this invention also include the mixture of alpha-anomer enriched formula 11 compound, preferably, the ratio of α:β in the mixture is more than 1:1.

In addition, this invention also provides a process for preparing formula 11 compound, it may adopt the following scheme 1:

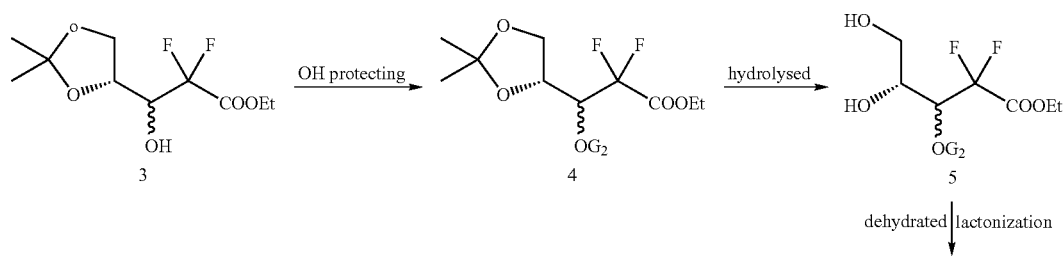

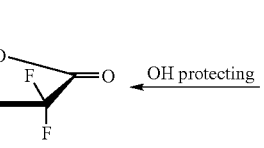
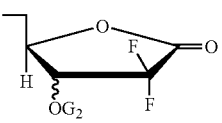
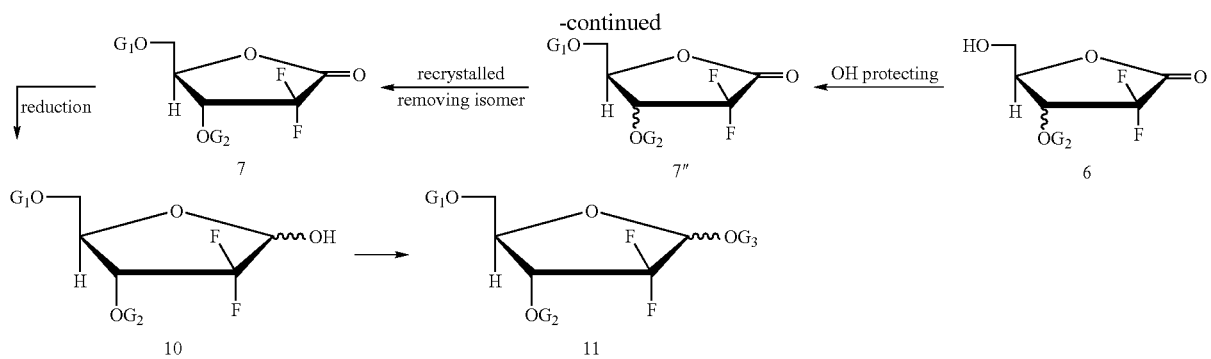

Firstly, in the present of acid scavenger, formula 3 compound reacts with an acylating agent in organic solvent to prepare hydroxyl group protected formula 4 compound. The acylating agent is preferably selected from benzoyl chloride, phenylacetyl chloride, biphenylcarbonyl chloride or biphenylacetyl chloride; the acid scavenger is preferably selected from pyridine, triethylamine and N,N-dimethyl-4-aminopyridine;

secondly, in the presence of trifluoroacetic acid and water, formula 4 compound in acetonitrile is hydrolyzed into formula 5 compound, then formula 5 is dehydrated and lactonized by refluxing, to get formula 6 compound;

thirdly, in the presence of acid scavenger, formula 6 compound reacts with acylating agent in an organic solvent to prepare 5'-hydroxyl group protected formula 7 compound, and was then purified by ethyl acetate and n-hexane to give pure erythro-structure thereof. The acylating agent is preferably selected from benzoyl chloride, phenylacetyl chloride, biphenylcarbonyl chloride or biphenylacetyl chloride; the acid scavenger is preferably selected from pyridine, triethylamine and N,N-dimethyl-4-aminopyridine;

finally, formula 7 compound is reduced into formula 10 compound in the presence of a reducing agent, then formula 10 compound is reacted with a sulphonating agent and acid scavenger to give alpha-anomer enriched ($\alpha$:$\beta$ up to 2-2.5:1) formula 11 compound, the said sulphonating agent is selected from C1-C4 alkylsulphonyl, arylsulphonyl, substituted alkylsulphonyl or substituted arylsulphonyl, preferably, methylsulphonyl, ethylsulphonyl, benzylsulphonyl, p-nitrobenzensulphonyl;

wherein, G1, G2 and G3 is defined as above.

Where the hydroxyl protected groups of formula 11 compound are the same, the following scheme 2 may be adopted to prepare it:

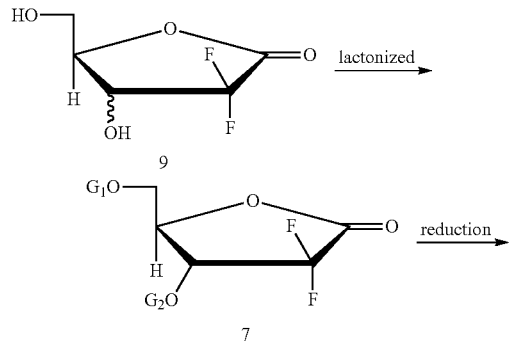

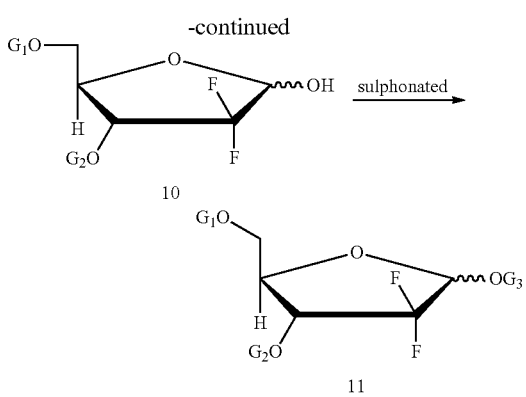

wherein, G1 and G2 are the same groups, and are defined as the following structure:

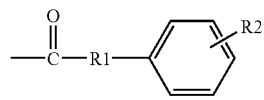

wherein, R1 is selected from the group consisting of C1-C3 alkyl, and null, preferably, null or —$CH_2$—, $CH_2CH_2$—;

R2 is selected from phenyl or substituted phenyl;

wherein the described substituted phenyl is the phenyl substituted by C1-C4 alkyl, or halogen (fluorine, chlorine, bromine, iodine);

G3 is selected from the group consisting of C1-C4 alkylsulphonyl, arylsulphonyl, substituted alkylsulphonyl or substituted arylsulphonyl, preferably, methylsulphonyl, benzylsulphonyl, p-toluenesulphonyl or p-nitrobenzenesulphonyl.

Firstly, formula 9 compound reacts with acylating agent in organic solvent in the present of acid scavenger to prepare the hydroxyl group protected formula 7 compound, which was then purified by toluene and n-hexane to get pure erythro-structure of compound 7. The acylating agent is preferably selected from benzoyl chloride, phenylacetyl chloride, biphenylcarbonyl chloride or biphenylacetyl chloride; the acid scavenger is preferably selected from pyridine, triethylamine or N,N-dimethyl-4-aminopyridine;

secondly, formula 7 compound is reduced into formula 10 compound in the present of a reducing agent, then formula 10 compound reacts with a sulphonating agent and acid scavenger to get alpha-anomer enriched ($\alpha$:$\beta$ up to 2-2.5:1) formula 11 compound.

In comparison with the prior art, the beneficial technical effect of this invention is demonstrated by:

1. the steps of preparing gemcitabine process have been reduced in the present invention:

In the present invention, by selecting suitable protecting groups, gemcitabine would be prepared in high yields and stereoselectivity, the drawbacks of multiple reactive steps and poor stereoselectivity in the prior art are overcome.

The condensation of a novel intermediate of compound 11 and protected cytosine has been used to yield beta isomer enriched compound 13 in the present invention. Formula II compound is added dropwise into the protected cytosine system during the condensation, to make sure that the protected cytosine is always reacting in high concentration. This allows the ratio (β:α) up to 3.5:1 of gemcitabine is prepared in the case of 2.5 mol equiv. ratio, which is much higher than the ratio of 1.3:1 in U.S. Pat. No. 5,371,210 which used 5 3.0 mol equiv., and as same as the ratio thereof using 20.0 mol resulting 4:1 isomer. The amount of cytosine applied is dramatically decreased in this invention, making the advantage obvious. Furthermore, in the comparison with WO 2006/071090, this invention has avoided the burden of using a large amount of solvent to get rid of 10 trimethylsilicane bromide after the condensation of bromides with protected cytosine, and is more friendly to the environment. After deprotection and forming salt, Gemcitabine hydrochloride has been prepared in 5 total reactive steps. (overall yields: 35.9%). The quality of final products is in accordance with requirement of USP28 and EP5.6.

In WO 2006/011713, compound XIV was prepared after compound 7 was reduced by t-butyl lithium aluminium hydride and reacted with biphenyloxyl phosphonyl chloride, then brominated into compound XV. However, 15~20 mol equiv of protected cytosine was required in order to obtain the ratio of isomer (α:β) 1:8.8 (89.9%). Gemcitabine hydrochloride was then prepared by deprotecting 20 and forming salt in 6 total reactive steps. (overall yields: 46.4%) (products purity: 99.97%). In contrast, the steps of reactions in the present invention are shorter, more convenient to be industrialized, and possesses higher maneuverability.

2. This invention simplifies the work up procedure making it more convenient for industrial production.

In the prior art for preparing gemcitabine most of the work up procedure applied column chromatography, which is not suitable for industrial production and resulted in increasing the cost of final products. The process of present invention for preparing gemcitabine has been improved by convenient work up procedures such as washing and recrystallization to obtain purer and higher ee value of products.

3. The conditions of reactions are much milder.

The conditions of reactions for the preparing process of gemcitabine in the present invention are much milder when compared to the prior art. Dispense with lower temperature than –20° C., the beta-anomer enriched key intermediates, i.e. formula 11 compound, could be obtained and hence lay a favorable foundation for finally preparing gemcitabine or its hydrochloride salt in high stereoselectivity.

DESCRIPTIONS OF THE DRAWINGS

EMBODIMENTS

Figure 1:
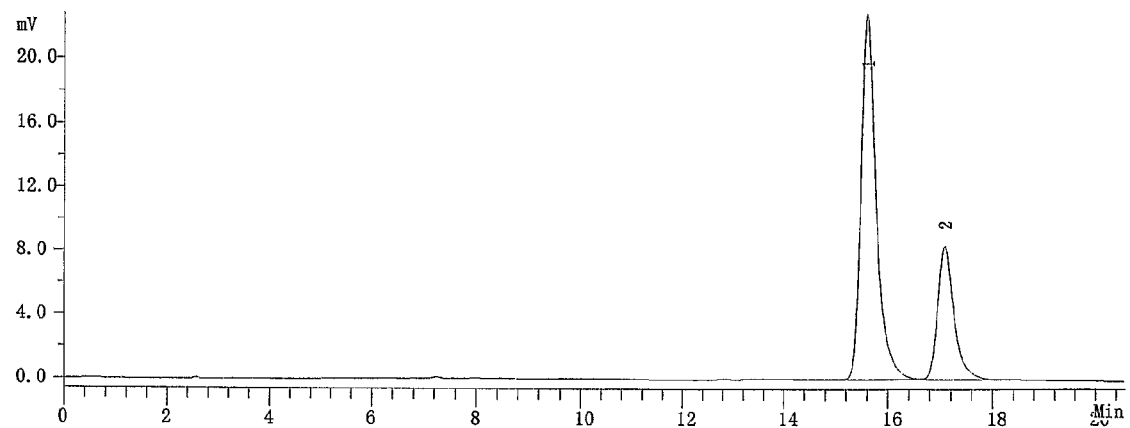
FIG. 1 shows the HPLC detecting results for 2-deoxy-2,2-difluoro-D-arabinofuranose-3,5-di-(4-phenyl)benzoate-1-methanesulphonate (α:β is 2.4:1).

To the technical persons skilled in the field, it should be understood that the following examples are only used for the invention to practise, however, modifications or replacements thereof according to the prior art should belong to the scopes of the invention.

Formula 11 compound and formula 13 compound are analyzed by HPLC, using Phenomenex Luna C18 (4.6×250 mm, 5 μm) column with aqueous solution of acetonitrile/1% triethylamine (adjust pH to 7.0 by phosphoric acid) as elution phase (80:20, v/v) and 1.0 ml/min of flowing rate.

Example 1

Preparation of 2,2-difluoro-3-(4-biphenylcarbonyl) oxo-3-(2,2-dimethyl-[1,3]dioxolan-4-yl)propionate (compound 4)

290.0 g of compound 3 was dissolved in 2900 ml of dichloromethane in the four-necks flask under the atmosphere of N$_2$, and then 117.2 ml of pyridine was added. The mixture was stirred for 10 mins. After 0.5 hours, 296.8 g of biphenylcarbonyl chloride was added in portions while the temperature was controlled between 20~25° C. After addition, the reaction was stirred at room temperature for 6 hours. It was washed with 950 ml 1N hydrochloric acid and 950 ml 5% NaHCO$_3$ solution and 950 ml of saturated NaCl solution subsequently. The organic phase was dried by anhydrous Na$_2$SO$_4$ and filtered. The filtrate was concentrated to dryness under vacuum to furnish 490.0 g (3R/3S=3:1). Yield: 98.9%.

Example 2

Preparation for 2-deoxy-2,2-difluoro-furanose-1-oxo-3-(4-phenyl)benzoate (compound 6)

495.0 g of 2,2-difluoro-3-(4-biphenylcarbonyl)oxo-3-(2, 2-dimethyl-[1,3]dioxolan-4-yl)propionate (compound 4) was added into 2500 ml acetonitrile and stirred until completely dissolved, then 14.5 ml of trifluoroacetic acid and 81 ml of distilled water was added. The whole mixture was refluxed for 3 hours with stirring, then changed to distill under atmospheric pressure, while each 500 ml solution of reaction had been distilled out, then 500 ml of anhydrous toluene was added. The distilling rate was controlled at 500 ml/15 mins until the temperature of reaction solution reached to 100° C. The reaction solution was concentrated under vacuum to dryness, recystallized with ethyl acetate and n-hexane to obtain 317.5 g of compound 6 (3R/3S=3:1). Yield: 80.0%.

Example 3

Preparation for D-erythro-2-deoxy-2,2-difluoro-furanose-1-oxo-5-benoyl-3-(4-phenyl)benzoate (compound 7)

To 5 L of four-necked flask 200 g of D-erythro-2-deoxy-2,2-difluoro-furanose-1-oxo-3-(4-phenyl)benzoate (compound 6) was completely dissolved in 2000 ml of dichloromethane under nitrogen, and 59.5 ml of pyridine was added and stirred for 10 minutes. Then, 96.0 g of benzoyl chloride in 480 ml of dichloromethane was added dropwise, after dropping completed, the reaction was stirred at room temperature for 6 hours. The mixture was washed with 950 ml of 1N hydrochloric acid, and 950 ml of 5% $NaHCO_3$ aqueous solution and 950 ml of saturated NaCl aqueous solution. The separated organic phase was dried over anhydrous $Na_2SO_4$ and filtered. The filtrate was then concentrated to dryness under vacuum, the residue was recrystallized with toluene and n-hexane to remove the isomer, 170 g of white solid of compound 7 (3R:3S=50:1) was obtained. Yield: 65.0%.

Figure 3:
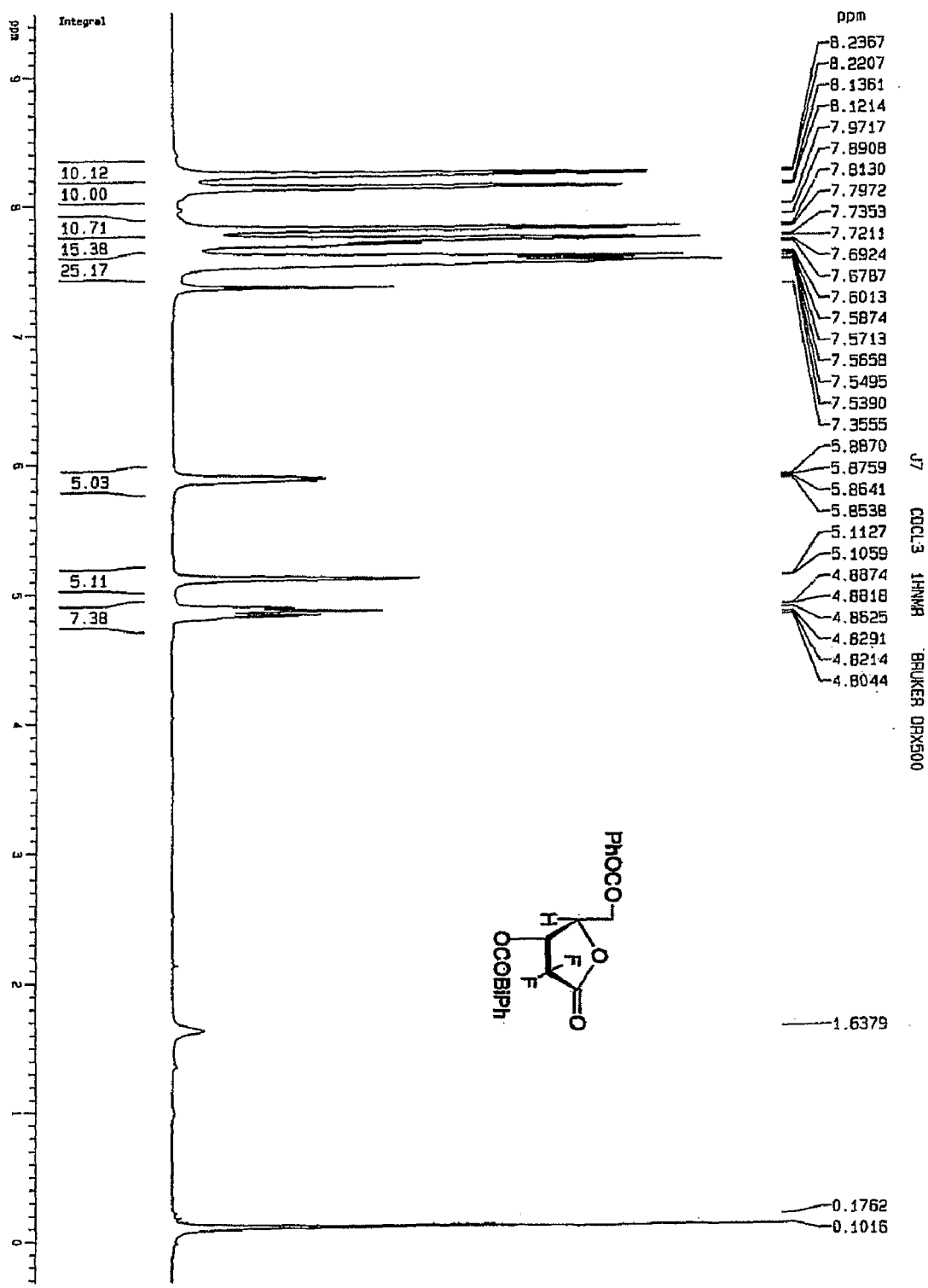
FIG. 3 shows the $^1$H-NMR (500 MHz, CDCl$_3$) spectrum for D-erythro-2-deoxy-2,2-difluoro-furanose-1-oxo-5-benzoyl-3-(4-phenyl)benzoate.
Figure 4:
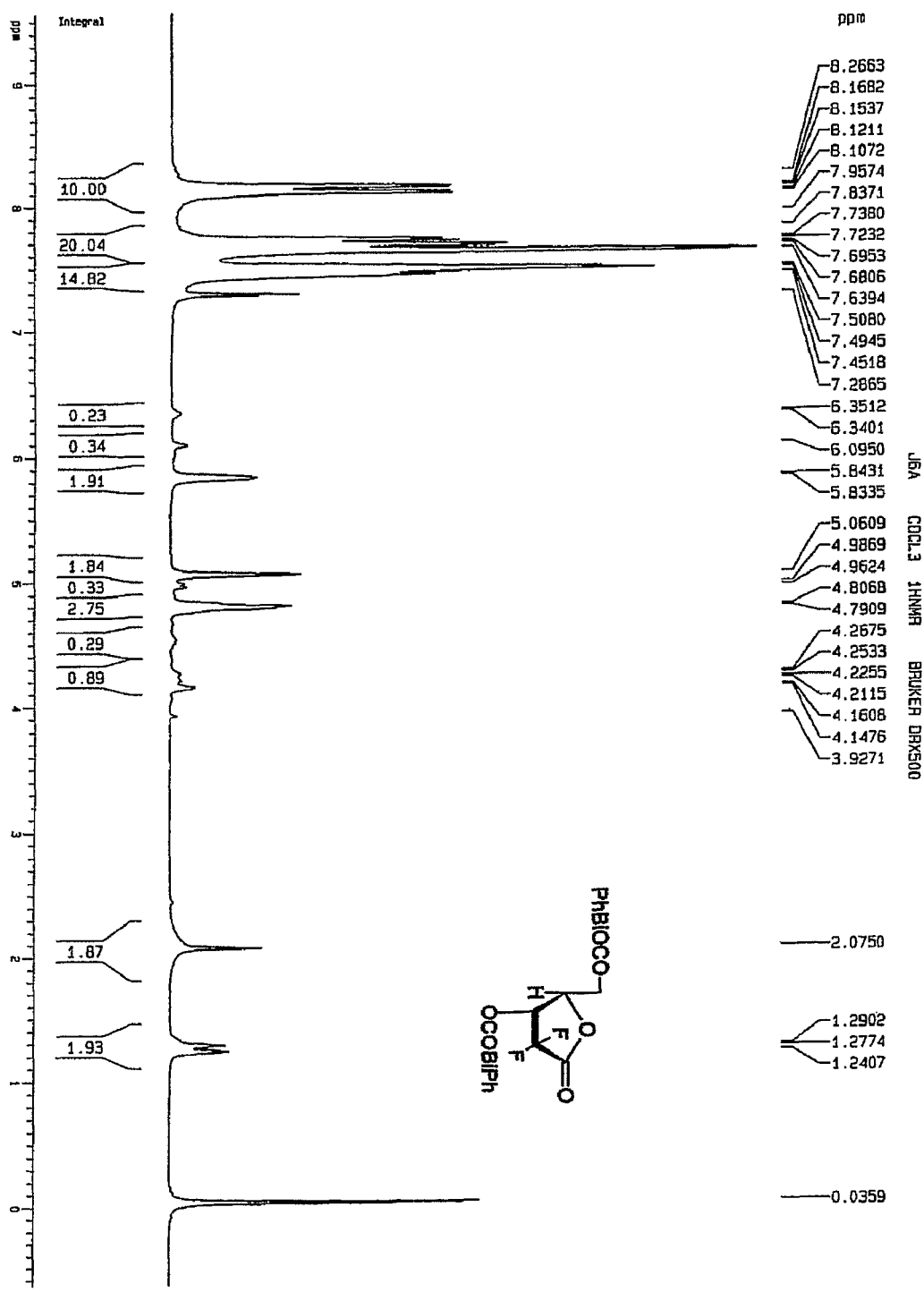
FIG. 4 shows the $^1$H-NMR (500 MHz, CDCl$_3$) spectrum for D-erythro-2-deoxy-2,2-difluoro-furanose-1-oxo-3,5-(4-phenyl)benzoate.

$^1$H-NMR (500 MHz, $CDCl_3$) (FIG. 3): δ8.23 (d, J=8.0 Hz, 2H), 8.13 (d, J=7.3 Hz, 2H), 7.79-7.35 (m, 10H), 5.88-5.85 (m, 1H), 5.12-5.10 (m, 1H), 4.88-4.80 (m, 2H).

The following compounds were prepared by the same procedure as described above:

D-erythro-2-deoxy-2,2-difluoro-furanose-1-oxo-5-phenylacetyl-3-(4-phenyl)benz oate (overall yield: 48.7%; 3R:3S=38:1).

D-erythro-2-deoxy-2,2-difluoro-furanose-1-oxo-5-benzoyl-3-phenylacetate (Total yield: 46.5%; 3R:3S=42:1).

D-erythro-2-deoxy-2,2-difluoro-furanose-1-oxo-5-benzoyl-3-(4-phenyl)phenylacetate (Total yield: 43.5%; 3R:3S=35:1).

D-erythro-2-deoxy-2,2-difluoro-furanose-1-oxo-5-phenylactyl-3-benzoate (Total yield: 45.0%; 3R:3S=43:1).

Example 4

Preparation of 1-oxo-2-deoxy-2,2-difluoro-furanose (compound 9)

To a four-necks flask 290 g of compound 3 were dissolved in 2700 ml of MeCN with stirring, 81 ml of distilled water and 14.5 ml of $CF_3COOH$ were added thereto, and the whole mixture was vigorously refluxed for 3 hours. It was then distilled under atmospheric pressure, 500 ml of anhydrous toluene was added after each 500 ml solution of reaction had been distilled out. The distilling rate was controlled at 500 ml/15 mins until the temperature of reaction solution reached to 100° C. Then the whole mixture was concentrated to dryness under vacuum to give 200 g of red brown oily compound 9 (3R/3S=3:1). Yield: 100.0%.

Example 5

Preparation of D-erythro-2-deoxy-2,2-difluoro-furanose-1-oxo-3,5-(4-phenyl)benzoate (compound 7)

To a solution of 200 g compound 9 in dichloromethane were added 34.8 g of DMAP and 257.5 ml of pyridine and stirred for 10 mins. 617.0 g of biphenylcarbonyl chloride was added in portions within 0.5 hour, while the temperature was controlled between 20~25° C. The reaction was stirred at room 20 temperature for 6 hours. Then the mixture was washed with 1800 ml of 1N hydrochloric acid, 1800 ml of 5% $NaHCO_3$ aqueous solution and 1800 ml of saturated NaCl aqueous solution. The separated organic layer was dried over anhydrous $Na_2SO_4$ and filtered. The filtrate was concentrated to dryness under vacuum, the residue was recrystallized with toluene and n-hexane to give 358 g 25 white solid of compound 7 (3R:3S=45:1). Yield: 57.0%.

The following compounds were prepared by the same method as described above:

D-erythro-2-deoxy-2,2-difluoro-furanose-1-oxo-3,5-di-(4-phenyl)benzoate (Total yield: 52.0%; 3R:3S=20:1).

D-erythro-2-deoxy-2,2-difluoro-furanose-1-oxo-3,5-diphenylacetate (Total yield: 55.5%; 3R:3S=46:1)

Example 6

Preparation of 2-deoxy-2,2-difluoro-D-arabinofuranose-3,5-di-(4-phenyl)benzoate-1-methanesulphonate (compound 11)

59.8 g of t-butyl lithium aluminium hydride was added into 630 ml of THF under nitrogen, and the mixture was cooled to −18° C. Then compound 7 was added in portions, maintained temperature of the reaction and stirred for 2 hours. 2500 ml of 1N HCl was slowly added, and the mixture was extracted with dichloromethane (600 ml×3), then organic layer was separated and washed with 10% sodium carbonate solution and water, and the separated organic layer was dried over anhydrous sodium sulphate. It was filtered, and the filtrate was concentrated to dryness under vacuum. 950 ml of dichloromethane was added to dissolve it, then 41.7 ml of triethylamine was added and cooled below 0-5° C. At this point, 23.2 ml solution of methylsulphonyl chloride in 50 ml dichloromethane was added dropwise, and maintained at 0-5° C. with stirring for 2 hours. It was then washed with 1N HCl, 10% sodium carbonate solution and water, the separated organic layer was dried over anhydrous sodium sulphate, filtered, and the filtrate was concentrated to dryness under vacuum, purified by alcohol to give 100.6 g of white solid (α:β=2.4:1) (HPLC results referred to FIG. 1) Yield: 85.0%.

Figure 5:
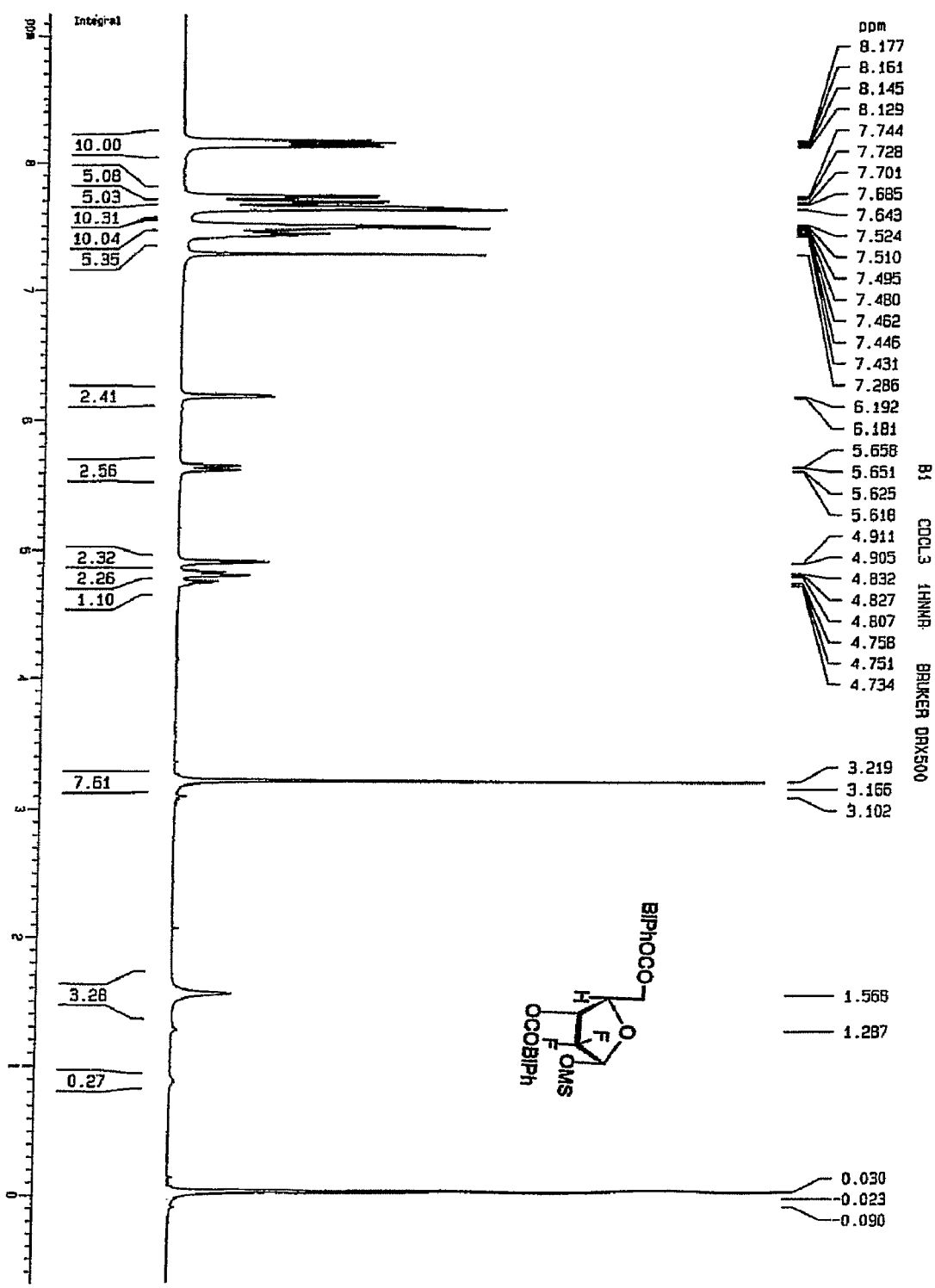
FIG. 5 shows the $^1$H-NMR (500 MHz, CDCl$_3$) spectrum for 1α-2-deoxy-2,2-difluoro-D-arabinofuranose-3,5-di-(4-phenyl)benzoate-1-methanesulphonate.
Figure 6:
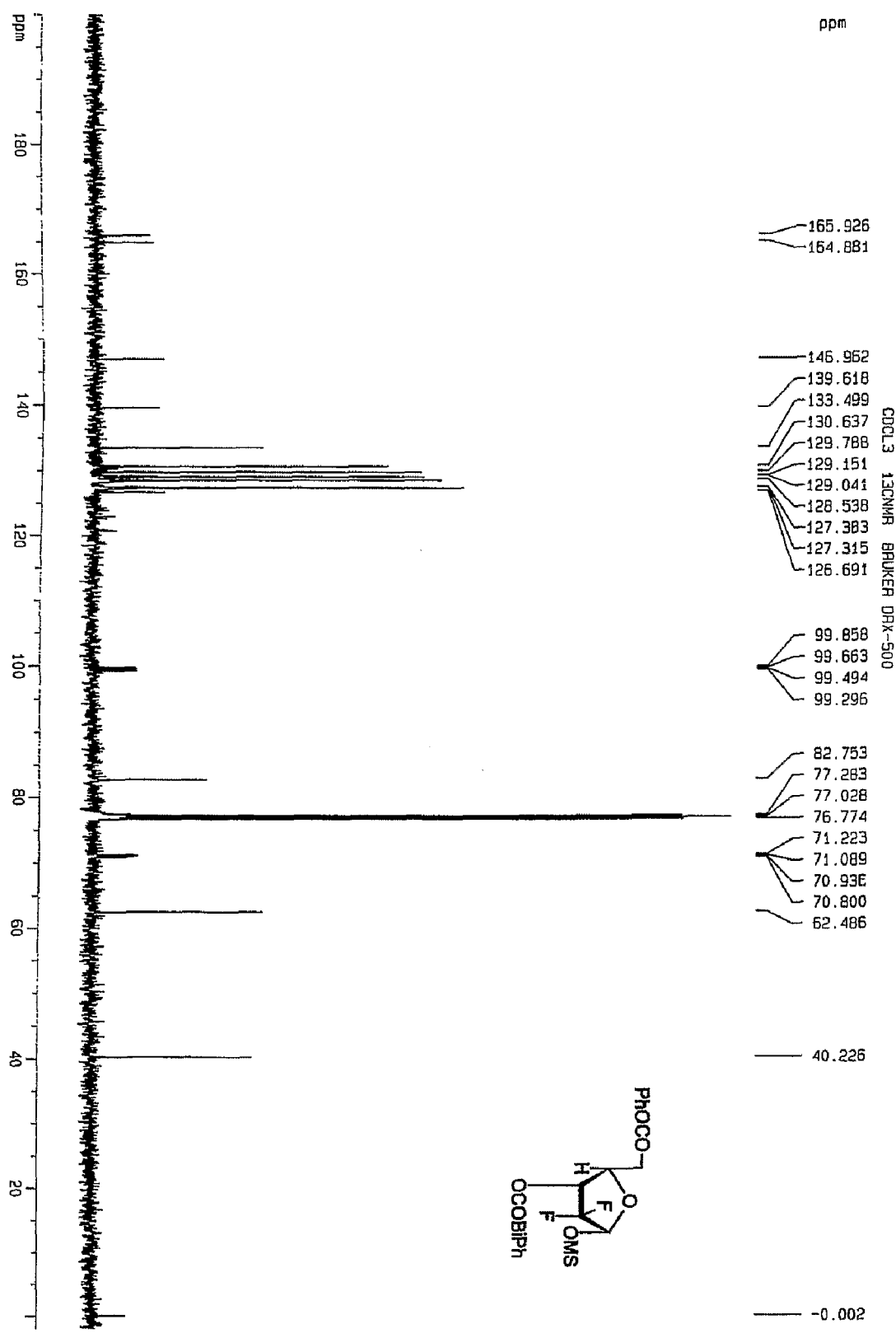
FIG. 6 shows the $^{13}$C-NMR ((125 MHz, CDCl$_3$)) spectrum for 1α-2-deoxy-2,2-difluoro-D-arabinofuranose-3,5-di-(4-phenyl)benzoate-1-methanesulphonate.

The product was purified by the column chromatography (ethyl actate and n-hexane as eluant) and pure α-anomer methanesulphonate and β-anomer methanesulphonate were obtained.

α-anomer methanesulphonate mp: 154.5~156.5° C.
$^1$H-NMR (500 MHz, $CDCl_3$) (FIG. 5):
δ8.17-8.13 (m, 4H), 7.74-7.64 (m, 8H), 7.52-7.43 (m, 7H), 6.18 (d, J=5.5 Hz, 1H), 5.63 (dd, J=3.5, 16.5 Hz, 1H), 4.91-4.73 (m, 2H), 3.22 (s, 3H),
$^{13}$C-NMR (125 MHz, $CDCl_3$) (FIG. 6):
δ66.5, 165.3, 147.4, 146.6, 140.2, 140.0, 131.0, 130.7, 129.4, 129.3, 128.8, 128.6, 128.2, 127.7, 127.6, 127.5, 127.0, 122 (q, CF2), 99.9, 83.0, 71.6, 62.9, 40.6.

Mass spectrum FAB 609 (M+1) elemental analysis $C_{32}H_{26}F_2O_8S$ calc.: C, 85.69%; H, 5.84%; F, 8.47%. found: C, 85.71%; H, 5.80%; F, 8.49%.

The following compounds were prepared by the same method as described above:

2-deoxy-2,2-difluoro-D-arabinofuranose-3,5-di-(4-phenyl)benzoate-1-ethanesulphonate (yield: 79.8%; α:β=2.2:1).

N,N-dimethyl-4-aminopyridine as acid scavenger:

2-deoxy-2,2-difluoro-D-arabinofuranose-3,5-di-(4-phenyl)benzoate-1-benzenesulphonate (yield: 6.5%; α:β=1.5:1).

2-deoxy-2,2-difluoro-D-arabinofuranose-3,5-di-(4-phenyl)benzoate-1-p-nitrobenzenesulphonate (yield: 69.0%; α:β=1.7:1).

Example 7

Preparation of 2-deoxy-2,2-difluoro-D-arabinofuranose-5-benzoate-3-(4-phenyl)benzoate-1-methanesulphonate (compound 11)

Figure 2:
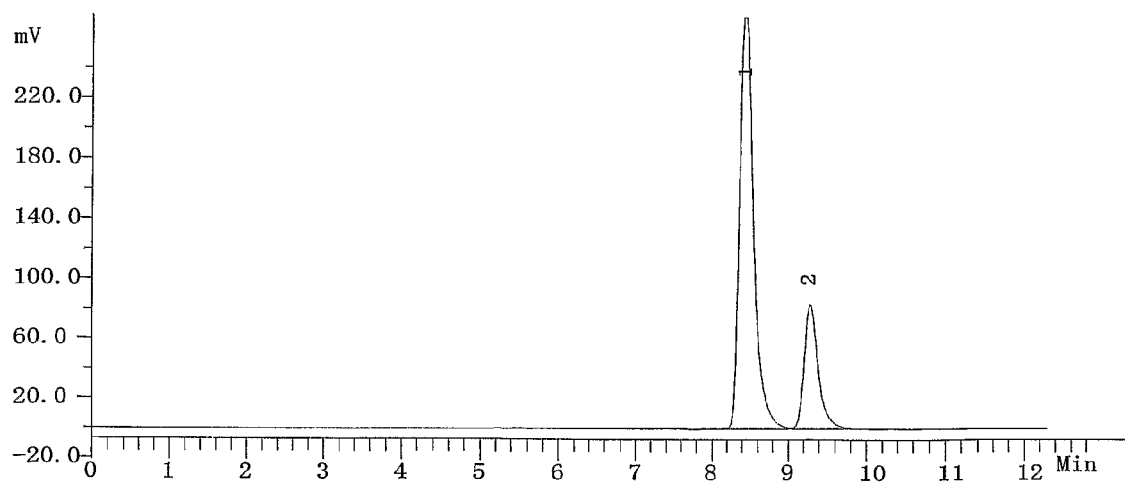
FIG. 2 shows the HPLC detecting results for 2-deoxy-2,2-difluoro-D-arabinofuranose-5-benzoate-3-(4-phenyl)benzoate-1-methanesulphonate (α:β is 2.5:1).

59.8 g of t-butyl lithium aluminium hydride was added into 600 ml of THF under nitrogen and the mixture was cooled to −18° C. Then compound 7 in 450 ml of THF was added dropwise while maintaining temperature of the reaction and stirred for 2 hours. 2400 ml of 1N HCl was added to quench the reaction, and the mixture was extracted with dichloromethane (500 ml×3). The combine organic layer was washed with 10% sodium carbonate solution and water, and then dried over anhydrous sodium sulphate. It was filtered, and the filtrate was concentrated to dryness under vacuum. The residue was dissolve in 950 ml of dichloromethane, then 41.7 ml of triethylamine was added and cooled below 0-5° C. At this point, 23.2 ml solution of methylsulphonyl chloride in 50 ml dichloromethane was added dropwise and maintained below 0-5° C. with stirring for 2 hours, washed with 1N HCl, 10% sodium carbonate solution and water. The separated organic layer was dried over anhydrous sodium sulphate, filtered, and the filtrate was concentrated to dryness under vacuum, purified by alcohol to give 88.2 g of white solid (α:β=2.5:1) (HPLC results referred to FIG. 2) Yield: 83.0%.

The product was purified by the column chromatography (ethyl actate and n-hexane as eluant) and pure α-anomer methanesulphonate and β-anomer methanesulphonate was obtained.

α-anomer methanesulphonate mp: 136.0~139.0° C.

Figure 7:
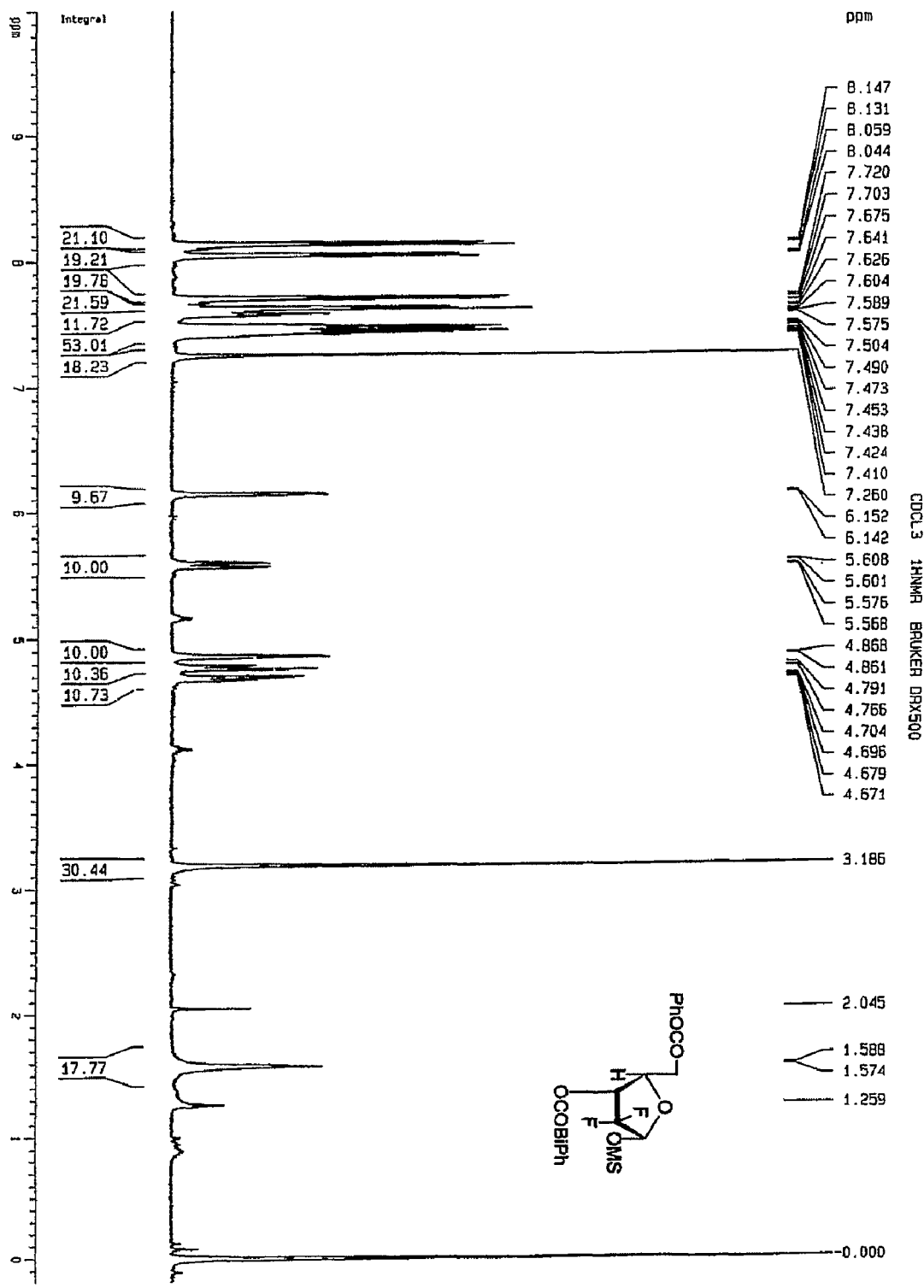
FIG. 7 shows the $^1$H-NMR (500 MHz, CDCl$_3$) spectrum for 1α-2-deoxy-2,2-difluoro-D-arabinofuranose-5-benzoate-3-(4-phenyl)benzoate-1-methanesulphonate.

$^1$H-NMR (500 MHz, CDCl$_3$) (FIG. 7):

δ8.11 (d, J=8.0 Hz, 2H), 8.04 (d, J=7.5 Hz, 2H), 7.72-7.41 (m, 10H), 7.60-7.57 (m, 1H), 6.15 (d, J=5.0 Hz, 1H), 5.60-5.56 (m, 1H), 4.79-4.67 (m, 2H), 3.18 (s, 3H)

Figure 8:
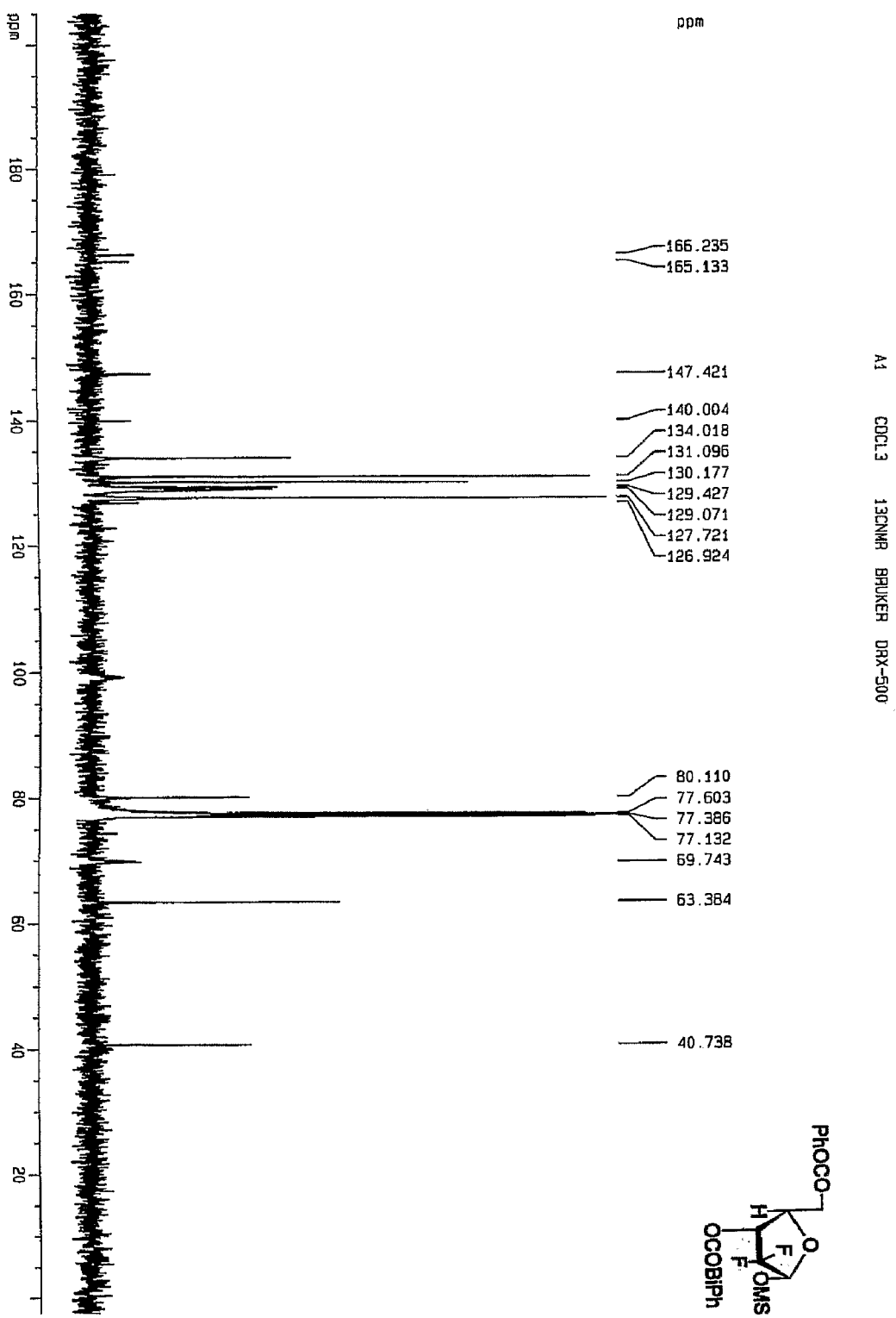
FIG. 8 shows the $^{13}$C-NMR ((125 MHz, CDCl$_3$)) spectrum for 1α-2-deoxy-2,2-difluoro-D-arabinofuranose-5-benzoate-3-(4-phenyl)benzoate-1-methanesulphonate.

$^{13}$C-NMR (125 MHz, CDCl$_3$) (FIG. 8):

δ165.9, 164.9, 146.9, 139.6, 133.5, 130.6, 129.8, 129.1, 129.0, 128.5, 127.4, 127.3, 126.1, 122 (q, CF2), 99.7, 82.7, 71.0, 62.5, 40.2

Mass spectrum FAB 533 (M+1); elemental analysis C$_{26}$H$_{22}$F$_2$O$_8$S calc.: C, 83.85%; H, 5.95%; F, 10.20%. found: C, 83.88%; H, 5.91%; F, 10.21%.

β-anomer methanesulphonate mp: 162.0~163.5° C.

Figure 9:
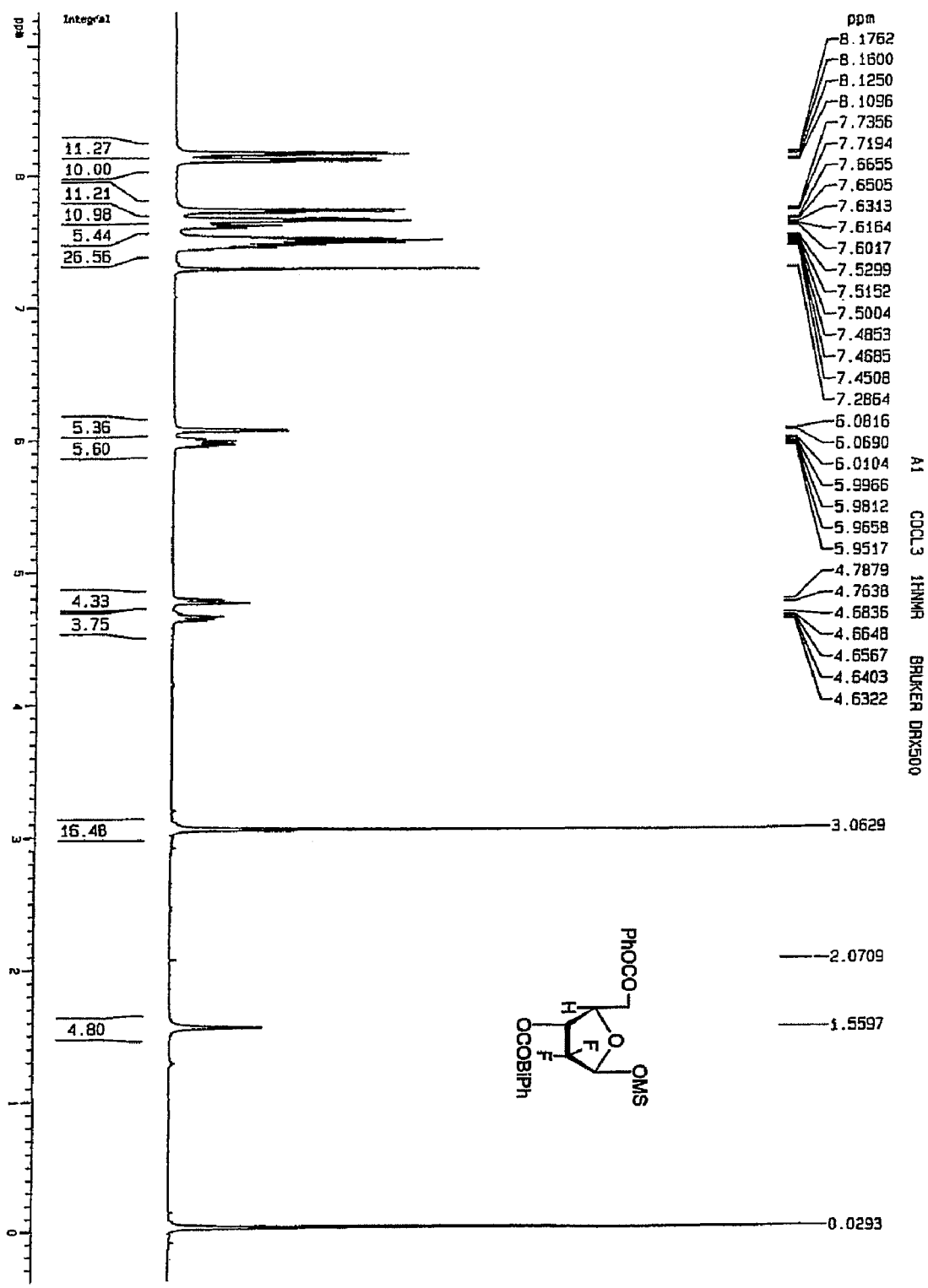
FIG. 9 shows the $^1$H-NMR (500 MHz, CDCl$_3$) spectrum for 1β-2-deoxy-2,2-difluoro-D-arabinofuranose-5-benzoate-3-(4-phenyl)benzoate-1-methanesulphonate.

$^1$H-NMR (500 MHz, CDCl$_3$) (FIG. 9):

δ8.16 (d, J=8.0 Hz, 2H), 8.11 (d, J=7.5 Hz, 2H), 7.73-7.45 (m, 10H), 7.60-7.57 (m, 1H), 6.07 (d, J=7.7 Hz, 1H), 6.01-5.95 (m, 1H), 4.78-4.62 (m, 2H), 3.06 (s, 3H)

Figure 10:
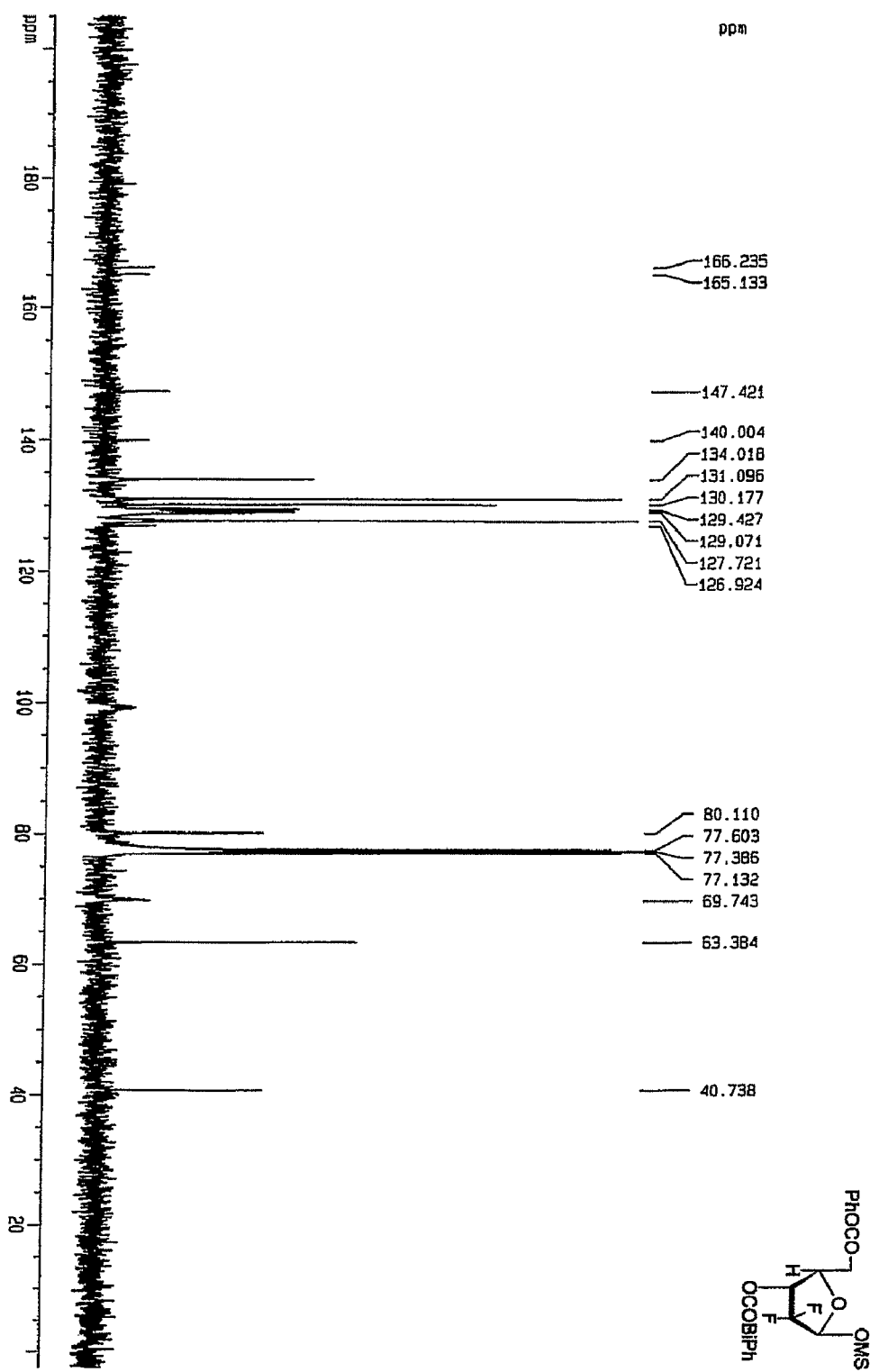
FIG. 10 shows the $^{13}$C-NMR ((125 MHz, CDCl$_3$)) spectrum for 1β-2-deoxy-2,2-difluoro-D-arabinofuranose-5-benzoate-3-(4-phenyl)benzoate-1-methanesulphonate.

$^{13}$C-NMR (125 MHz, CDCl$_3$) (FIG. 10):

δ166.2, 165.1, 147.4, 140.0, 134.0, 131.1, 130.0, 129.4, 129.0, 127.7, 126.9, 122 (q, CF2), 99.7, 80.1, 69.7, 63.4, 40.7

The following compounds were prepared by the same procedure as described above:

2-deoxy-2,2-difluoro-D-arabinofuranose-5-benzoate-3-(4-phenyl)benzoate-1-ethanesulphonate (yield: 80.2%; α:β=2.1:1).

N,N-dimethyl-4-aminopyridine as acid scavenger:

2-deoxy-2,2-difluoro-D-arabinofuranose-5-benzoate-3-(4-phenyl)benzoate-1-benzylsulphonate (yield: 69.3%; α:β=1.6:1).

2-deoxy-2,2-difluoro-D-arabinofuranose-5-benzoate-3-(4-phenyl)benzoate-1-p-nitrobenzenesulphonate (yield: 70.5%; α:β=1.7:1).

Example 8

Preparation of 1-(2'-deoxy-2',2'-difluoro-3,5-di-(4-phenyl)benzoyl-D-arabinofuranose-4-aminopyrimidine-2-one (compound 13)

100 g of cytosine was added into 550 ml of toluene under nitrogen, then 0.5 g of ammonium sulphate and 283 ml of hexamethyldisilazane were added. The whole mixture was refluxed for 3 hours, the mixture was concentrated to dryness under vacuum, and the residue was dissolved in 600 ml of toluene. The resulting solution was heated to 100° C. and 219 g of 2-deoxy-2,2-difluoro-D-arabinofuranose-3,5-di-(4-phenyl)benzoate-1-methanesulphonate (compound 11) (α:β=2.4:1) in 1100 ml of toluene solution was added dropwise. Within 5 hours, after dropping completed, it was refluxed for 3 hours (α:β=1:1.8). The temperature of reaction was cooled to 40° C., the mixture was washed with water 10 (500 ml×3), 500 ml of 5% sodium carbonate solution and saline, and the organic layer was concentrated to dryness. It was recrystallized with alcohol to remove a anomer and 119.0 g of the titled compound (α:β=1:40) was obtained. Yield: 53.0%.

The following compounds were prepared by the same method as described above:

1-(2'-deoxy-2',2'-difluoro-3,5-(4-phenyl)benzoyl-D-arabinofuranose-4-acetylaminopyrimidine-2-one (yield: 49.5%; α:β=1:35)

Example 9

Preparation of 1-(2'-deoxy-2',2'-difluoro-5-benzoyl-3-(4-phenyl)benzoate-D-arabinofuranose-4-aminopyrimidine-2-one (compound 13)

400 g of cytosine was added into 2200 ml of toluene, 2.0 g of ammonium sulphate and 1130 ml of hexamethyldisilazane was added under nitrogen and then refluxed for 3 hours. The mixture was concentrated to dryness under vacuum, and the residue was dissolved in 2400 ml of toluene and heated to 100° C. 122 g of 2-deoxy-2,2-difluoro-D-arabinofuranose-5-benzoyl-3-(4-phenyl)benzoate-1-methanesulphonate (compound 11) (α:β=2.5:1) in 600 ml of toluene solution was added dropwise thereto within 3 hours, after finishing dropping, refluxed for 3 hours (α:β=1:1.8). The temperature of reaction was cooled to 60° C., then 780 ml of methanol was added and stirred for 10 minutes. Then 780 ml 2N HCl was added dropwise and a large amount of solid appeared. After maintaining the temperature and stirring for 20 minutes, the mixture was cooled to room temperature and filtered, the filter cake was washed with 2N HCl (1000 ml×3) to remove excess cytosine, then purified with alcohol to remove a anomer to give 78.7 g of the titled compound (α:β=1:35). Yield: 55.0%.

β-anomer compound 13 mp: 247.5-248.5° C.

Figure 11:
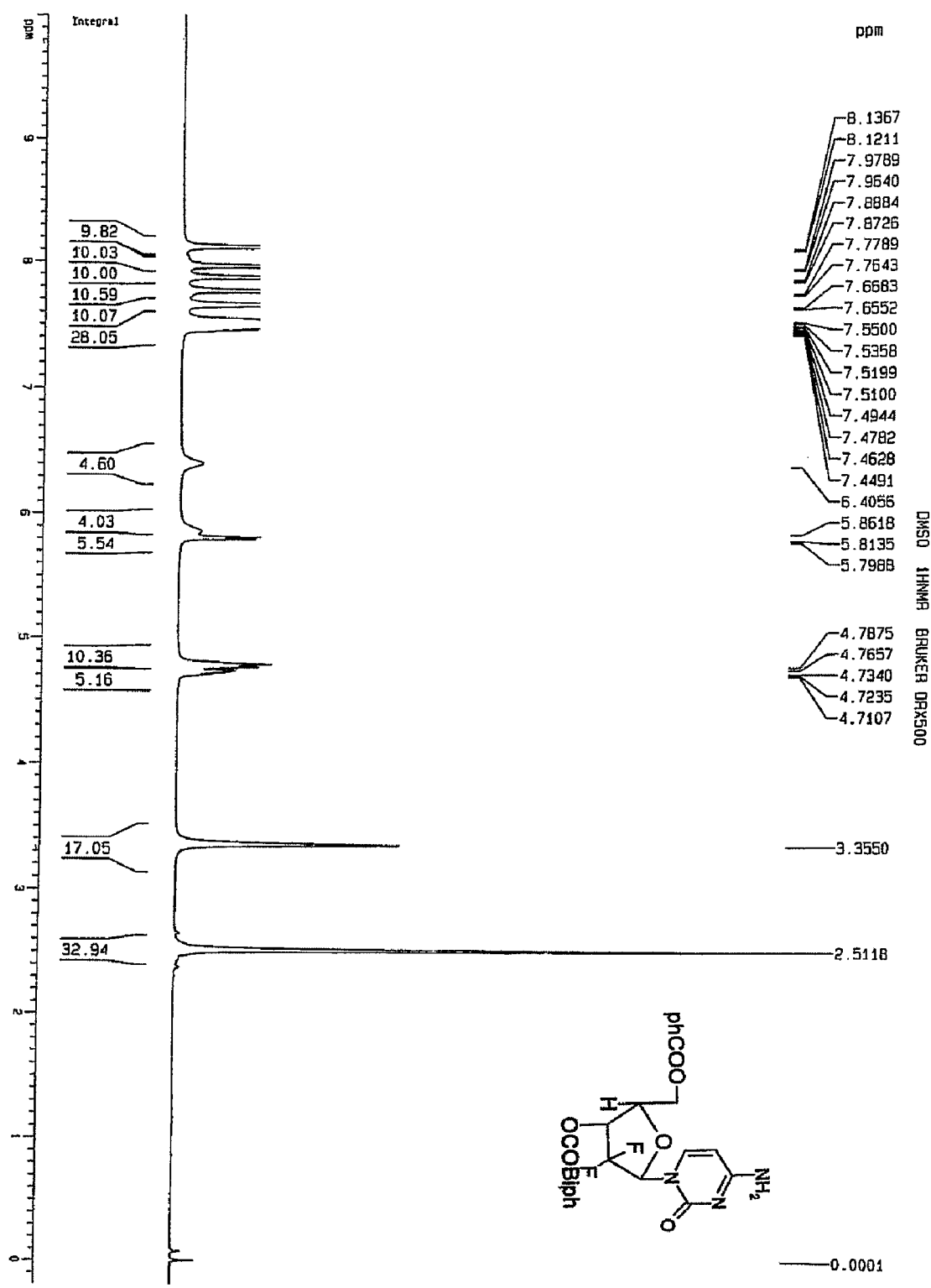
FIG. 11 shows the $^1$H-NMR (500 MHz, CDCl$_3$) spectrum for 1-(2'-deoxy-2',2'-difluoro-5-benzoyl-3-(4-phenyl)benzoate-D-arabinofuranose-4-D-arabinofuranose-4-aminopyrimidine-2-one.

$^1$H-NMR. (500 MHz, CDCl$_3$) (FIG. 11):

δ8.13 (d, J=7.5 Hz, 2H), 7.97 (d, J=7.5 Hz, 2H), 7.87 (d, J=7.5 Hz, 2H), 7.77 (d, J=7.3 Hz, 2H), 7.66 (d, J=6.5 Hz, 2H), 7.55-7.44 (m, 6H), 6.40 (s, br, 1H), 5.86 (s, br. 1H), 4.78-4.71 (m, 3H).

The following compounds were prepared by the same method as described above:

1-(2'-deoxy-2',2'-difluoro-5-benzoyl-3-(4-phenyl)benzoate-D-arabinofuranose-4-acetylaminopyrimidine-2-one (yield: 51.5%; α:β=1:40)

Example 10

Preparation for 2'-deoxy-2',2'-difluorocytidine (compound 2)

Compound 13 was added into methanol/ammonia solution under nitrogen and stirred at room temperature overnight. The mixture was concentrated to dryness under reduced pressure and dissolved in water, then extracted by ethyl acetate. Finally, the aqueous phase was concentrated to dryness to produce 18.7 g gemcitabine (purity: 97.0%, ee 99.5%). Yields: 88.5%.

Example 11

Preparation for gemcitabine hydrochloride

Compound 2 was dissolved in isopropyl alcohol and cooled to 0~5° C., and conc. hydrochloric acid was added to adjust pH to 2, maintained the temperature to let the crystal grow for 2 hours, filtered. The crystal was washed with 100 ml isopropyl alcohol to furnish 51.2 g of gemcitabine hydrochloride (purity: 99.8%), yields: 90.0%.

The invention claimed is:

1. A process for preparing beta-anomer enriched gemcitabine, comprising:
carrying out the following reaction:

[Reaction scheme: Compound 11 + Compound 12 → Compound 13]

wherein, the substitutions of G1 and G2 are independently the radicals defined by the following structure:

[Structure: —C—R1—phenyl—R2]

wherein, R1 is selected from the group consisting of C1-C3 alkyl and null;
R2 is selected from the group consisting of hydrogen, C1-C4 alkyl, phenyl and substituted phenyl;
and with the provision that for at least one of G1 and G2, R2 is phenyl or substituted phenyl;
the said substituted phenyl is the one substituted by C1-C4 alkyl, or halogen;
G3 is selected from the group consisting of alkylsulfonyl, arylsulfonyl, substituted alkylsulfonyl and substituted arylsulfonyl;
G4 and G5 are independently selected from the group consisting of C1-C7 trialkylsilyl, t-butoxycarbonyl, carbobenzoxyl, 9-fluoroenylmethylcarbonyl (Fmoc), formyl, acetyl, propionyl, isopropionyl, butyryl, isobutyryl, and pivaloyl;
wherein carrying out the reaction includes:
preparing a first solution of a compound of formula 12 in an organic solvent selected from the group consisting of 1,2-dichloroethane, toluene, xylene, substituted benzene, anisole, diphenyl ether, substituted diphenyl ether, and a mixture thereof;
heating the first solution to a temperature of about 100-150° C.;
preparing a second solution of a compound of formula 11 in the organic solvent, where the molar ratio of the compound of formula 12 to the compound of formula 11 is about 2.5 to 15;
adding the first solution dropwise to the second solution over a period of about 3 to 7 hours; and
heating the resultant reaction solution at reflux for about 3-6 hours.

2. The process of claim 1, wherein the compound of formula 11 is alpha-anomer enriched, and the resulting compound of formula 13 is beta-anomer enriched.

3. The process of claim 1, wherein $G_2$ is biphenylcarbonyl.

4. The process of claim 3, wherein $G_1$ and $G_2$ are biphenylcarbonyl, G3 is methylsulphonyl.

5. The process of any one of claims 1 to 4, wherein for the said reaction the first solution is heated to a temperature of about 110-150° C.; and the resultant reaction solution temperature is refluxed for about 5 hours.

6. The process of claim 1, wherein the reaction temperature is from 110 to 130° C.

7. The process of any one of claims 1 to 4, which further includes the following deprotecting reaction:

[Reaction scheme: Compound 13 → Compound 2]

in a methanol/ammonia solution.

8. The process of claim 7, which further includes treating compound 2 with hydrochloric acid to produce gemcitabine hydrochloride.

* * * * *